(12) United States Patent
Yarrusso, Jr.

(10) Patent No.: US 7,717,300 B1
(45) Date of Patent: May 18, 2010

(54) AEROSOL SPRAYING DEVICE

(76) Inventor: Daniel P. Yarrusso, Jr., 1222 Trent Dr., Murrells Inlet, SC (US) 29576

( * ) Notice: Subject to any disclaimer, the term of this patent is extended or adjusted under 35 U.S.C. 154(b) by 848 days.

(21) Appl. No.: 11/465,310

(22) Filed: Aug. 17, 2006

(51) Int. Cl.
*B67D 7/84* (2010.01)

(52) U.S. Cl. .................. 222/174; 222/473; 43/125; 43/132.1; 248/128; 239/531; 239/532

(58) Field of Classification Search ............. 222/174, 222/473; 43/125, 132.1; 248/128; 239/531–532
See application file for complete search history.

(56) References Cited

U.S. PATENT DOCUMENTS

| | | | |
|---|---|---|---|
| 1,534,734 A | | 4/1925 | Porter |
| 3,856,209 A | * | 12/1974 | Hickson .................. 239/532 |
| 3,949,440 A | * | 4/1976 | Guerra .................... 7/148 |
| 4,092,000 A | * | 5/1978 | Offutt, III .............. 239/532 |
| 4,457,472 A | * | 7/1984 | Geberth, Jr. ............ 239/532 |
| 4,881,699 A | * | 11/1989 | Emura ..................... 242/248 |
| 4,886,191 A | * | 12/1989 | Yoshitomi ............... 222/174 |
| 5,099,539 A | * | 3/1992 | Forester .................. 15/144.3 |
| 5,307,959 A | * | 5/1994 | Bedore et al. ............ 222/174 |
| 5,518,148 A | * | 5/1996 | Smrt ...................... 222/174 |
| D382,326 S | | 8/1997 | Geeting |
| 5,904,273 A | * | 5/1999 | Aspacher et al. ....... 222/402.15 |
| 6,205,702 B1 | | 3/2001 | Ammons |
| 6,450,423 B1 | * | 9/2002 | Gurule .................... 239/531 |
| 6,581,326 B1 | * | 6/2003 | Smith ..................... 43/132.1 |
| 6,789,705 B2 | * | 9/2004 | Drew ...................... 222/174 |
| 2005/0086852 A1 | | 4/2005 | Williams et al. |
| 2005/0108922 A1 | | 5/2005 | Bianchini |

* cited by examiner

*Primary Examiner*—Kevin P Shaver
*Assistant Examiner*—Andrew P Bainbridge

(57) ABSTRACT

An aerosol spraying device for actuating an aerosol can to spray an insecticide from the aerosol in a desired location includes a pole including a first end engaging an aerosol can. A canister support is coupled to the pole adjacent the first end. The canister support extends under a portion of the aerosol can to support the aerosol can. An actuating assembly is coupled to the pole. The actuating assembly engages a nozzle of the aerosol can to actuate the nozzle and release contents of the aerosol can when the actuating assembly is actuated.

1 Claim, 5 Drawing Sheets

AEROSOL SPRAYING DEVICE

BACKGROUND OF THE INVENTION

1. Field of the Invention

The present invention relates to canister actuating devices and more particularly pertains to a new canister actuating device for actuating an aerosol can to spray an insecticide from the aerosol in a desired location.

2. Description of the Prior Art

The use of canister actuating devices is known in the prior art. The prior art commonly teaches poles with a canister mounted to the pole where a portion of the pole is retracted to actuate the canister. While these devices fulfill their respective, particular objectives and requirements, the need remains for a device that has certain improved features that allows an aerosol can to be actuated through a separate actuating assembly to maintain positioning of the device. Additionally, the device should allow the user to be positioned at an angle from an area being sprayed to inhibit spray dripping onto the user.

SUMMARY OF THE INVENTION

The present invention meets the needs presented above by generally comprising a pole including a first end engaging an aerosol can. A canister support is coupled to the pole adjacent the first end. The canister support extends under a portion of the aerosol can to support the aerosol can. An actuating assembly is coupled to the pole. The actuating assembly engages a nozzle of the aerosol can to actuate the nozzle and release contents of the aerosol can when the actuating assembly is actuated.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
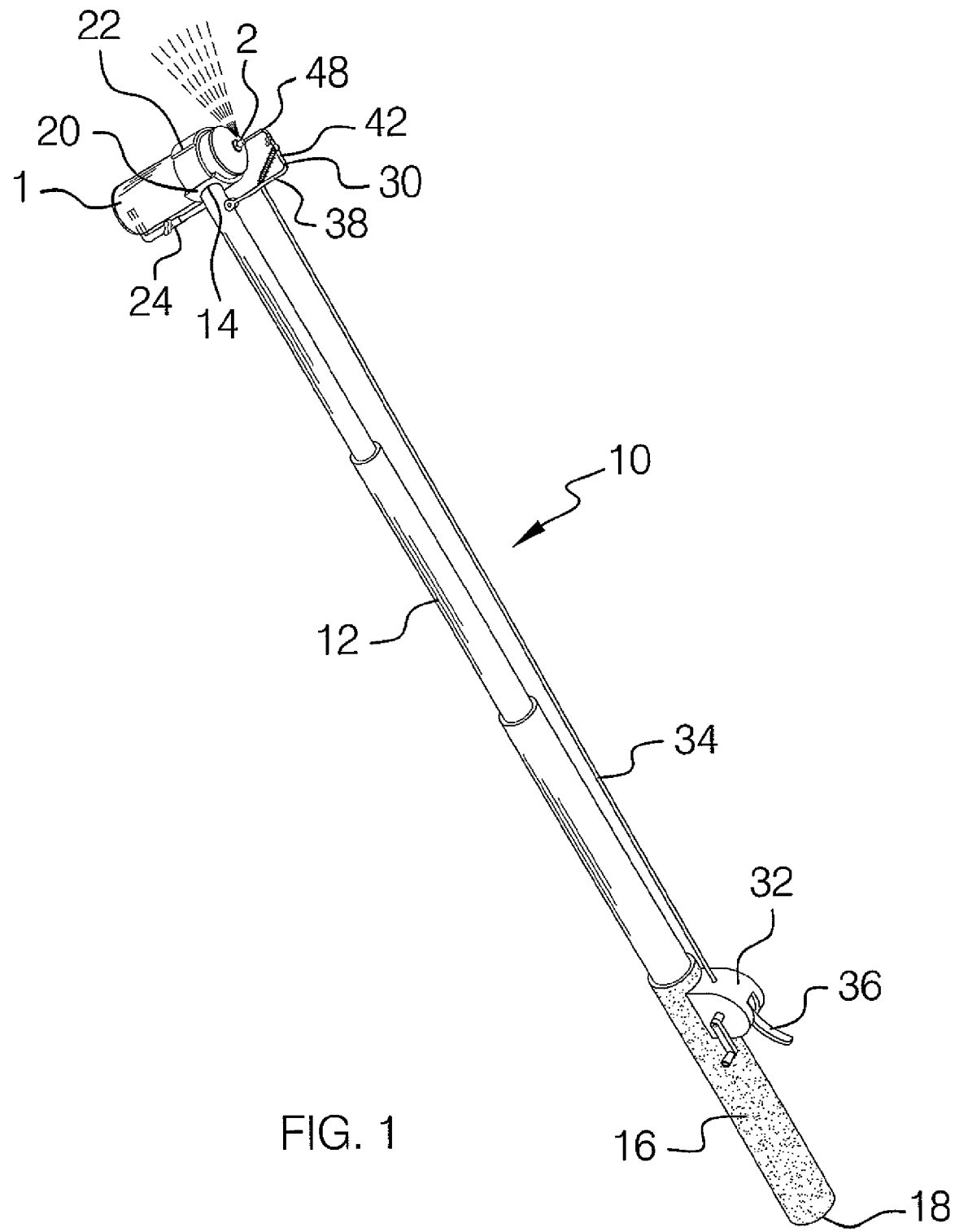
FIG. 1 is a perspective view of an aerosol spraying device according to the present invention.
Figure 2:
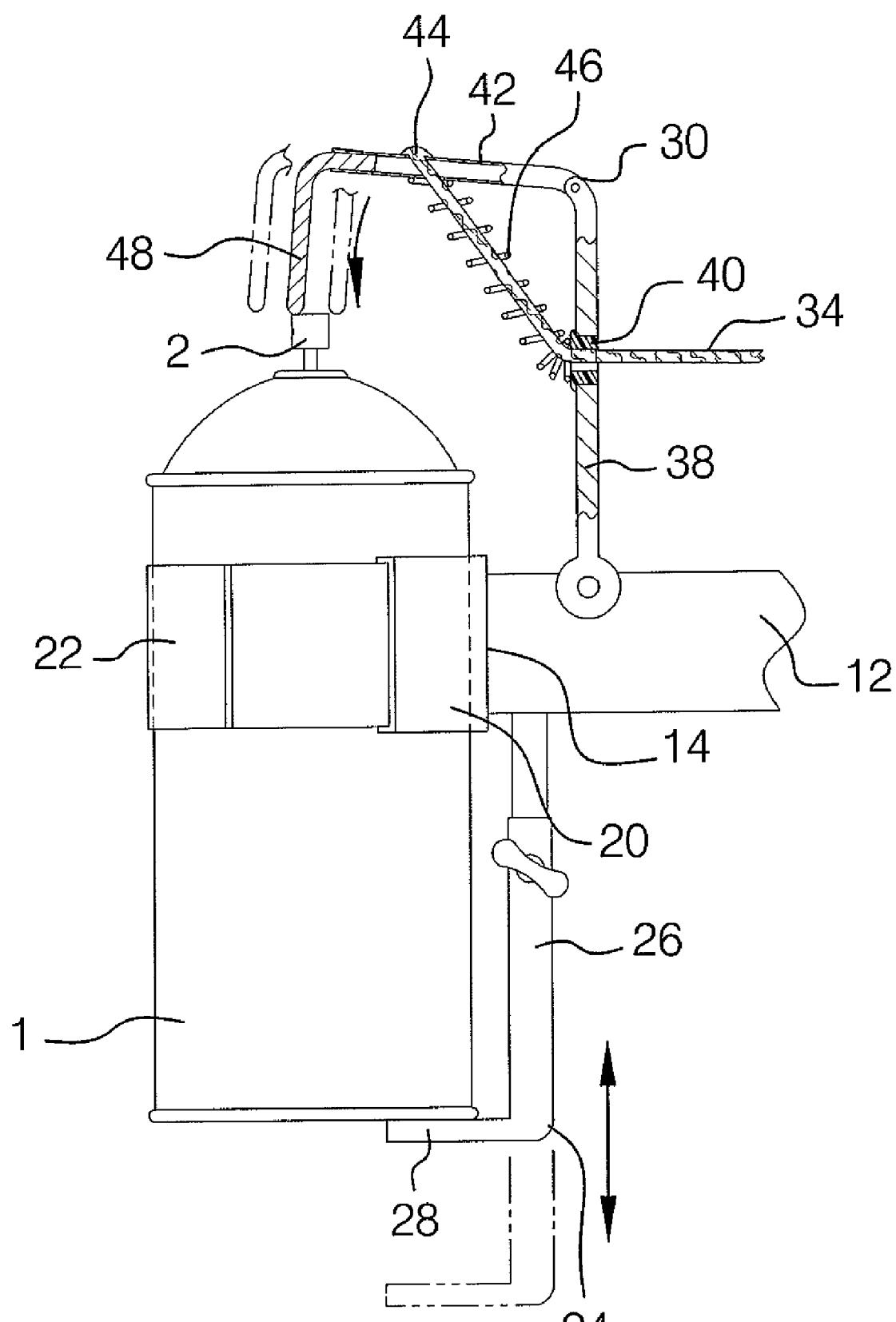
FIG. 2 is a side view of a first end of the pole of the present invention.
Figure 3:
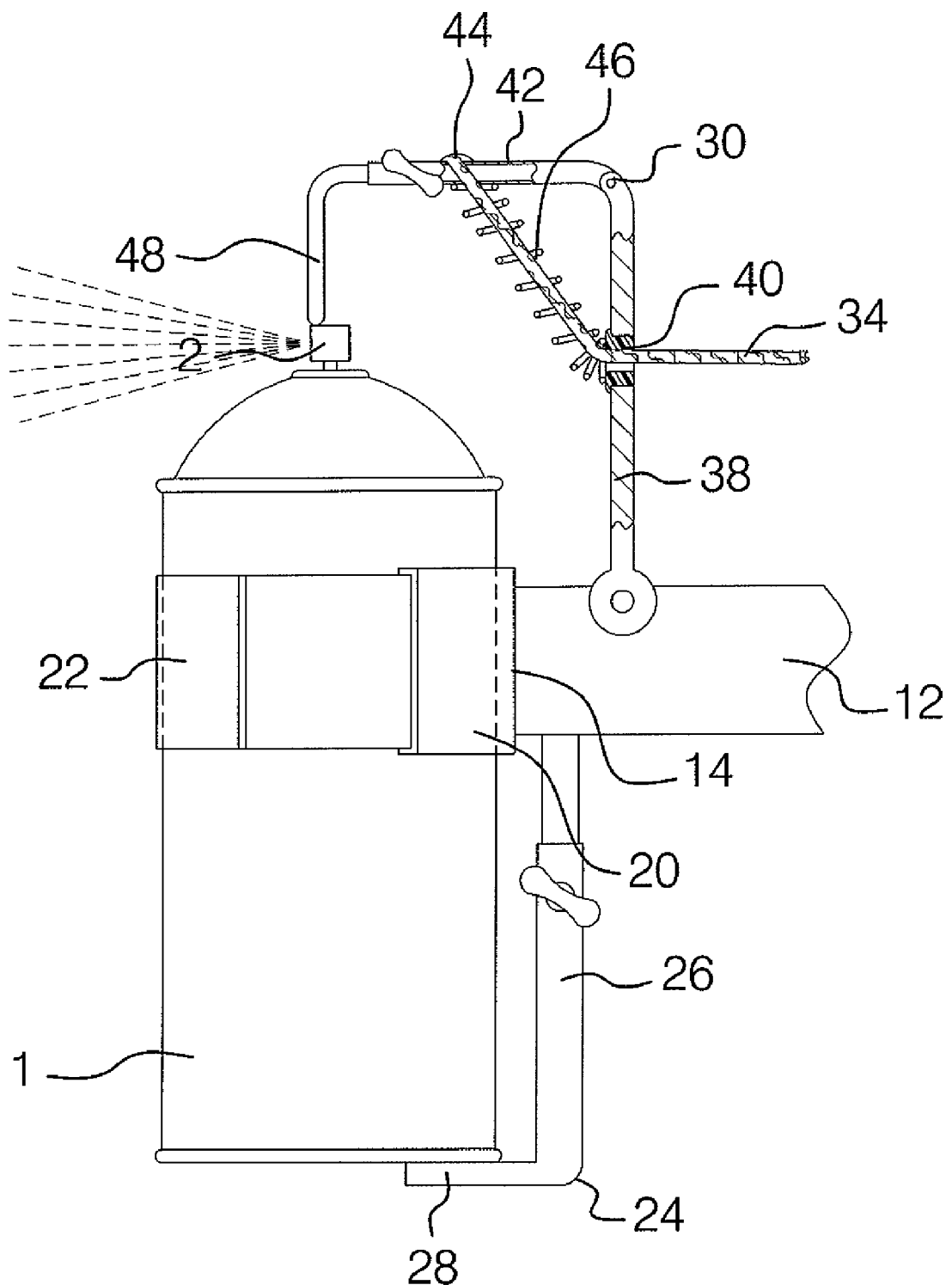
FIG. 3 is a side view of the first end of the pole of the present invention with the actuating assembly actuating the nozzle.
Figure 4:
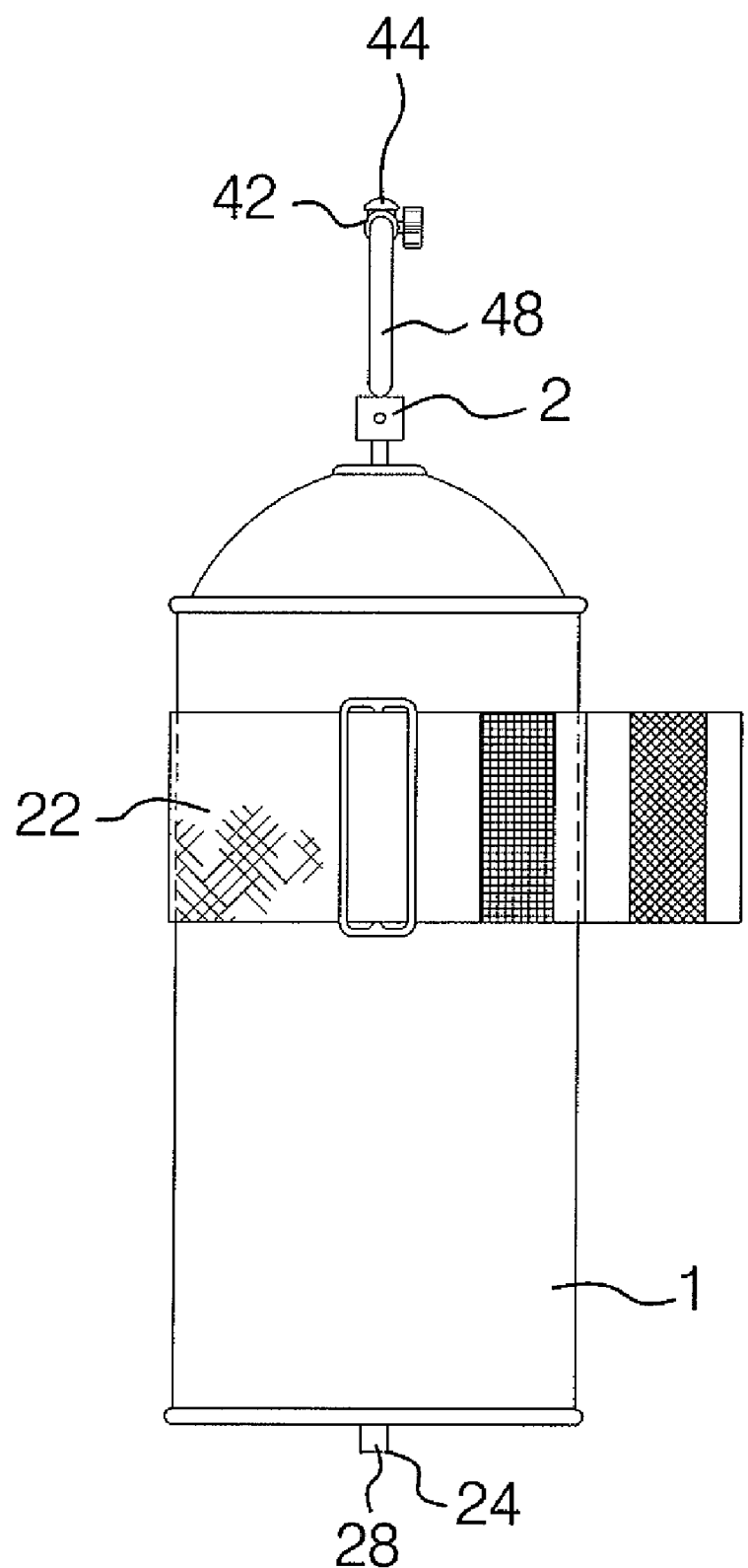
FIG. 4 is an end view of the present invention.
Figure 5:
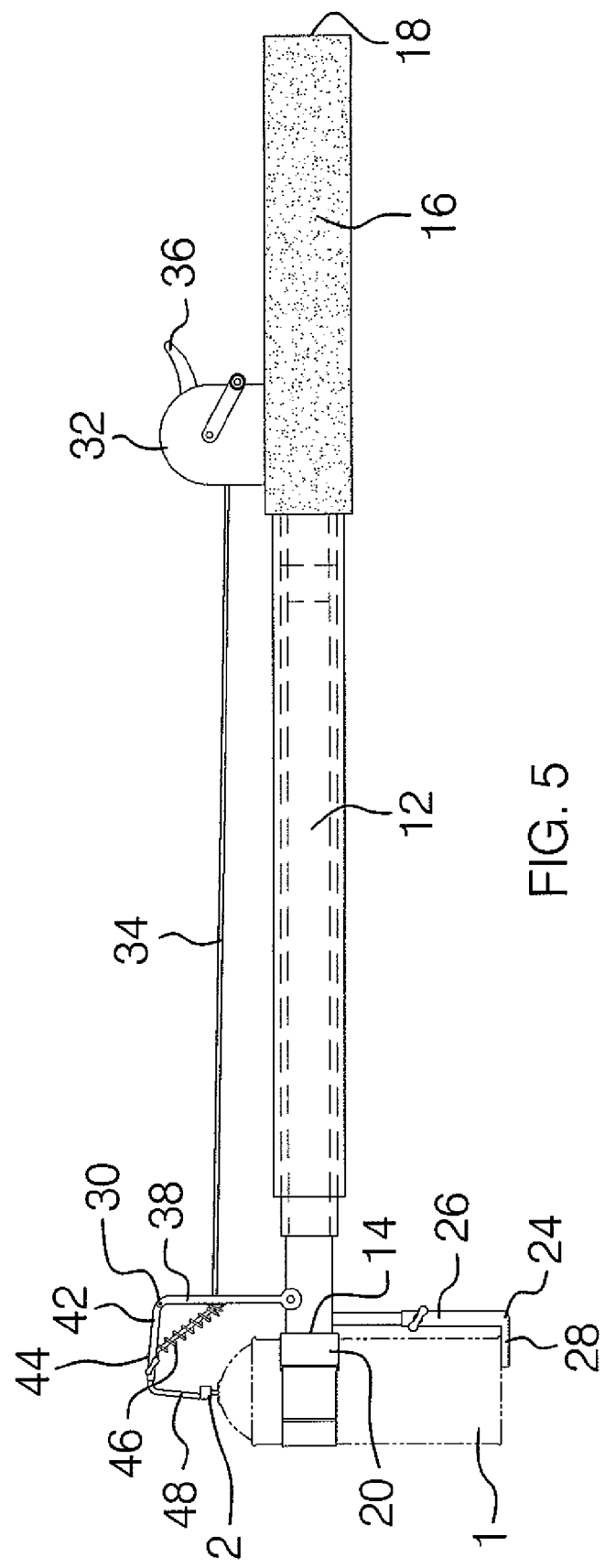
FIG. 5 is a side view of the present invention with the pole retracted.

With reference now to the drawings, and in particular to FIGS. 1 through 5 thereof, a new canister actuating device embodying the principles and concepts of the present invention and generally designated by the reference numeral 10 will be described.

As best illustrated in FIGS. 1 through 5, the aerosol spraying device 10 generally comprises a pole 12 including a first end 14 engaging an aerosol can 1. The pole 12 includes a grip 16 positioned adjacent a second end 18 of the pole 12 opposite the first end 14. The pole 12 is telescopic to permit a length of the pole 12 to be adjusted. A cradle 20 is coupled to the first end 14 of the pole 12. The cradle 20 receives a portion of the aerosol can 1 to maintain a desired orientation of the aerosol can 1 with respect to the pole 12. A strap 22 is coupled to and extendable across the cradle 20 opposite the pole 12. The strap 22 is extendable around the aerosol can 1 to secure the aerosol can 1 in the cradle 20.

A canister support 24 is coupled to the pole 12 adjacent the first end 14. The canister support 24 extends under a portion of the aerosol can 1 to support the aerosol can 1. The canister support 24 includes an extension bar 26 coupled to and extending downwardly from the first end 14. The canister support 24 includes a support arm 28 coupled to the extension bar 26 opposite the pole 12. The support arm 28 extends orthogonally from the extension bar 26 and under the aerosol can 1 to support the aerosol can 1. The extension bar 26 is telescopic to permit a length of the extension bar 26 to be adjusted to accommodate various sized aerosol cans 1.

An actuating assembly 30 is coupled to the pole 12. The actuating assembly 30 engages a nozzle 2 of the aerosol can 1 to actuate the nozzle 2 and release contents of the aerosol can 1 when the actuating assembly 30 is actuated. The actuating assembly 30 includes a reel 32 coupled to the pole 12 adjacent the second end 18. A cable 34 is operationally coupled to and extendable from the reel 32. The reel 32 is selectively actuated to wind the cable 34 into the reel 32. The cable 34 extends along a portion of a length of the pole 12. An actuator lever 36 is operationally coupled to the reel 32. The actuator lever 36 actuates the reel 32 to retract a portion of the cable 34 into the reel 32. The reel 32 releases the portion of the cable 34 retracted into the reel 32 when the actuator lever 36 is released.

The actuating assembly 30 also includes a stanchion 38 coupled to the pole 12 adjacent the first end 14. The stanchion 38 extends upwardly from the pole 12. The cable 34 extends through the stanchion 38. A bushing 40 extends through the stanchion 38 and is positioned around the cable 34 extending through the stanchion 38. The bushing 40 inhibits damage between the stanchion 38 and the cable 34 when the cable 34 moves through the stanchion 38.

The actuating assembly 30 additionally includes an actuating bar 42 pivotally coupled to the stanchion 38 opposite the pole 12. A terminal end 44 of the cable 34 is coupled to the actuating bar 42. The actuating bar 42 is pivoted downwardly when the cable 34 is retracted into the reel 32. The actuating bar 42 is telescopic to permit a length of the actuating bar 42 to be selectively adjusted. A biasing member 46 is positioned around the cable 34 and extends between the stanchion 38 and the actuating bar 42. The biasing member 46 biases the actuating bar 42 upwardly when the cable 34 is released from the reel 32. A depressing bar 48 is coupled to the actuating bar 42 opposite the stanchion 38. The depressing bar 48 extends downwardly from the actuating bar 42 to engage the nozzle 2 of the aerosol can 1. The depressing bar 48 depresses the nozzle 2 of the aerosol can 1 when the actuating bar 42 is pivoted downwardly.

In use, the aerosol can 1 is positioned in the cradle 20 and the strap 22 is extended around the aerosol can 1 to secure the aerosol can 1 in the cradle 20. The length of the extension bar 26 is adjusted so that the support arm 28 abuts the bottom of the aerosol can 1. The length of the actuating bar 42 is adjusted so that the depressing bar 48 is positioned over the nozzle 2 of the aerosol can 1. The actuator lever 36 is actuated to draw the portion of the cable 34 into the reel 32 and force the depressing bar 48 onto the nozzle 2 and release the contents of the aerosol can 1. The actuator is then released to allow the reel 32 to release the portion of the cable 34 drawn into the reel 32 and the biasing member 46 forces the actuating bar 42 upwardly and removes the depressing bar 48 from the nozzle 2.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An aerosol spraying device for actuating an aerosol can, said device comprising:

a pole including a first end engaging the aerosol can, said pole including a grip positioned adjacent a second end of said pole opposite said first end, said pole being telescopic to permit a length of said pole to be adjusted;

a cradle being coupled to said first end of said pole, said cradle receiving a portion of the aerosol can to maintain a desired orientation of the aerosol can with respect to said pole;

a strap being coupled to and extendable across said cradle opposite said pole, said strap being extendable around the aerosol can to secure the aerosol can in said cradle;

a canister support being coupled to said pole adjacent said first end, said canister support extending under a portion of the aerosol can to support the aerosol can, said canister support including an extension bar coupled to and extending downwardly from said first end, said canister support including a support arm being coupled to said extension bar opposite said pole, said support arm extending orthogonally from said extension bar and under the aerosol can to support the aerosol can, said extension bar being telescopic to permit a length of said extension bar to be adjusted to accommodate various sized aerosol cans;

an actuating assembly being coupled to said pole, said actuating assembly engaging a nozzle of the aerosol can to actuate the nozzle and release contents of the aerosol can when said actuating assembly is actuated, said actuating assembly comprising:

a reel being coupled to said pole adjacent said second end;

a cable being operationally coupled to and extendable from said reel, said reel being selectively actuated to wind said cable into said reel, said cable extending along a portion of a length of said pole;

an actuator lever being operationally coupled to said reel, said actuator lever actuating said reel to retract a portion of said cable into said reel, said reel releasing the portion of said cable retracted into said reel when said actuator lever is released;

a stanchion being coupled to said pole adjacent said first end, said stanchion extending upwardly from said pole, said cable extending through said stanchion;

a bushing extending through said stanchion and being positioned around said cable extending through said stanchion, said bushing inhibiting damage between said stanchion and said cable when said cable moves through said stanchion;

an actuating bar being pivotally coupled to said stanchion opposite said pole, a terminal end of said cable being coupled to said actuating bar, said actuating bar being pivoted downwardly when said cable is retracted into said reel, said actuating bar being telescopic to permit a length of said actuating bar to be selectively adjusted;

a biasing member being positioned around said cable and extending between said stanchion and said actuating bar, said biasing member biasing said actuating bar upwardly when said cable is released from said reel; and a depressing bar being coupled to said actuating bar opposite said stanchion, said depressing bar extending downwardly from said actuating bar to engage the nozzle of the aerosol can, said depressing bar depressing the nozzle of the aerosol can when said actuating bar is pivoted downwardly.

* * * * *